(12) United States Patent  
Guilford et al.

(10) Patent No.: US 8,349,359 B2
(45) Date of Patent: Jan. 8, 2013

(54) LIPOSOMAL FORMULATION FOR ORAL ADMINISTRATION OF GLUTATHIONE (REDUCED)

(75) Inventors: F. Timothy Guilford, Palo Alto, CA (US); Brian Charles Keller, Pitsburg, CA (US)

(73) Assignee: Your Energy Systems, LLC, Palo Alto, CA (US)

( * ) Notice: Subject to any disclaimer, the term of this patent is extended or adjusted under 35 U.S.C. 154(b) by 2001 days.

(21) Appl. No.: 11/163,979

(22) Filed: Nov. 6, 2005

(65) Prior Publication Data

US 2006/0099244 A1 May 11, 2006

Related U.S. Application Data

(60) Provisional application No. 60/522,785, filed on Nov. 7, 2004, provisional application No. 60/597,041, filed on Nov. 6, 2005.

(51) Int. Cl.
*A61K 9/127* (2006.01)

(52) U.S. Cl. ...................................... 424/450

(58) Field of Classification Search .................. 424/450
See application file for complete search history.

(56) References Cited

U.S. PATENT DOCUMENTS

| 6,011,067 | A | 1/2000 | Hersh |
| 6,470,894 | B2 | 10/2002 | Hersh |
| 6,764,693 | B1 * | 7/2004 | Smith ........................... 424/450 |
| 2002/0025313 | A1 * | 2/2002 | Micklus et al. ............. 424/130.1 |
| 2003/0059462 | A1 * | 3/2003 | Barenholz et al. ............. 424/450 |
| 2004/0022841 | A1 * | 2/2004 | Hassan et al. .................. 424/450 |
| 2004/0170560 | A1 * | 9/2004 | Fossheim et al. ............. 424/1.29 |
| 2006/0171935 | A1 * | 8/2006 | Abeliovich et al. ......... 424/93.21 |

FOREIGN PATENT DOCUMENTS

| EP | 0834301 A1 | 4/1998 |
| FR | 2609393 | 7/1988 |
| WO | WO-94/13265 | 6/1994 |
| WO | WO-02/091866 A1 | 11/2002 |

OTHER PUBLICATIONS

Junghans et al in Free Rad. Res. vol. 33, pp. 801-808, 2000.*
Wendel in Biochemical Pharmacol. vol. 31, pp. 3607-3611, 1981.*
Bharat in Biochem Pharmacol. vol. 64, pp. 1037-1048, 2002.*
Jellinger in Drugs Aging, vol. 14 (2), pp. 115-140, 1999 Sechi in Pro. Neuropsychopharmacol.Biol Psychiatry, vol. 20, pp. 1159-1170, 1996.*
Kiwada, H, "Application of Synthetic Liposomes Based on Acyl Amino Acids or Acyl Peptides as Drug Carriers. I. Their Preparation and Transport of Glutathione into the Liver," 35 Chem. Pharm.Bull. 2935 (Pharm Socy. of Japan, Tokyo, 1987).
Wendell A, "Drug-Induced Lipid Peroxidation in Mice-III: Glutathione Content of Liver, Kidney, and Spleen after Intravenous Administration of Free and Liposomally Entrapped Glutathione," 31 Biochem. Pharm. 3607-3611 (Pergamon Press Ltd. Great Britain 1982).
Jurima-Romet, M., "Lung Uptake of Liposome-entrapped glutathione after Intratracheal Administration," 43 J.Pharm. Pharmacol. 6-10 (Wiley London 1991).
Suntres Z, Incorporation of alpha-tocopherol in liposomes promotes the retention of liposome-encapsulated glutathione in the rat lung, 46 J.Pharm.Pharmacol. 23-28 (Pharm. Press England 1994).PMID 8201524.

* cited by examiner

*Primary Examiner* — Gollamudi Kishore
(74) *Attorney, Agent, or Firm* — Brooke Schumm, III; Daneker, McIntire, Schumm et al.; Lee M. Pederson

(57) ABSTRACT

The invention is a composition administrable orally to provide systemic glutathione (reduced) and a method for providing systemic glutathione by oral administration of glutathione (reduced) in a liposome encapsulation. The administration of a therapeutically effective amount of oral liposomal glutathione (reduced) results in improvement of symptoms in disease states related to glutathione deficiency such as Parkinson's disease and cystic fibrosis. Compounds enhancing the effect of the liposomal glutathione are contemplated such as Selenium, EDTA, carbidopa, and levodopa.

16 Claims, No Drawings

LIPOSOMAL FORMULATION FOR ORAL ADMINISTRATION OF GLUTATHIONE (REDUCED)

CONTINUATION DATA

This application claims priority of U.S. Provisional Application No. 60/522,785 entitled Liposomal Formulation for Oral Administration of Glutathione (reduced) filed on Nov. 7, 2004, and claims priority of U.S. Provisional Application No. 60/597,041 filed on Nov. 6, 2005 entitled Liposomal Formulation for Oral Administration of Glutathione (Reduced), and is a continuation-in-part of those applications.

This application is also continuation-in-part of pending U.S. application Ser. No. 11/230,277 filed 20 Sep. 2005 entitled "Combination And Method Using EDTA Combined With Glutathione In The Reduced State Encapsulated In A Liposome To Facilitate The Method Of Delivery Of The Combination As An Oral, Topical, Intraoral Or Transmucosal, For Anti-Thrombin Effect And For Anti-Platelet Aggregation And Measurement Of Efficacy" which claims benefit of provisional application filed on or about 20 Sep. 2004 and is a continuation-in-part of pending U.S. application Ser. No. 10/289,934 entitled "Systemic Administration Of NAC As An Adjunct In The Treatment Of Bioterror Exposures Such As Anthrax, Smallpox Or Radiation And For Vaccination Prophylaxis, And Use In Combination With DHEA For The Treatment Of Smallpox And Other Viruses" filed on Nov. 7, 2002, which claims benefit of a provisional application No. 60/338,267 filed Nov. 9, 2002 and a provisional application 60/371,590 filed Apr. 11, 2002.

SUMMARY OF INVENTION

The invention is a composition of glutathione (reduced) in a liposome constructed to stabilize the glutathione in a physiologically active state which can be orally administered and delivers a therapeutically effective amount of glutathione (reduced) to improve symptoms in disease states by transfer of the glutathione into the cells of the body, and method of manufacture of the same. Previous art did not enable oral administration of glutathione (reduced) in a therapeutically effective way. The invention is also a method of encapsulating glutathione (reduced) in a liposome constructed to stabilize the glutathione in a physiologically active state and to enable the oral administration of a therapeutically effective amount of glutathione (reduced) to improve symptoms in disease states by transfer of the glutathione into the cells of the body. Compounds enhancing the effect of the liposomal glutathione are contemplated such as Selenium, EDTA, carbidopa and levodopa.

TECHNICAL FIELD

The invention relates to the field of delivery of a nutrient substance, glutathione in the biochemically-reduced form, in a liposomal preparation that allows the novel delivery mode of oral delivery of glutathione (reduced) in a sufficient amount to improve the condition of a disease state related to glutathione deficiency. The delivery may also be accomplished via absorption across the mucosa of the nose, mouth, gastrointestinal tract, after topical application for transdermal, or intravenous infusion.

BACKGROUND

The tripeptide L-glutathione (GSH) (gamma-glutamyl-cysteinyl-glycine) is well known in biological and medical studies to serve several essential functions in the cells of higher organisms such as mammals. It is functional when it appears in the biochemical form known as the reduced state (GSH). When oxidized, it forms into a form known as a dimer (GSSG).

Glutathione in the reduced state (GSH) functions as an antioxidant, protecting cells against free-radical mediated damage, a detoxifying agent by transporting toxins out of cells and out of the liver, and a cell signal, particularly in the immune system.

A deficiency of glutathione (reduced) may lead to damage to cells and tissues through several mechanisms including the accumulation of an excess of free radicals which causes disruption of molecules, especially lipids causing lipid peroxidation, and which combined with toxin accumulation will lead to cell death. These mechanisms are often referred to as oxidation stress as general term. The lack of sufficient glutathione in the reduced state relative to the oxidized state may be due to lack of production of glutathione (reduced) or an excess of the materials such as toxins that consume glutathione (reduced). The lack of glutathione (reduced) may manifest as a systemic deficiency or locally in specific cells undergoing oxidation stress.

Deficiency of glutathione in the reduced state contributes to oxidative stress, which plays a key role in aging and the pathogenesis of many diseases such as Cystic fibrosis
Liver disease
Parkinson's disease
Alzheimer's disease
Heart attack and Stroke
Diabetes
Viral disease
Free radical damage from nuclear, biological or chemical insult
Free radical damage from bacterial infection
Immune system modulation after vaccination The use of the term "glutathione" or "glutathione (reduced)" will refer to glutathione in the reduced state.

Replacing glutathione in deficient states has been difficult because of the lack of direct absorption of glutathione after oral administration. Glutathione is a water-soluble peptide. This characteristic of glutathione is thought to prevent its absorption into the system after oral ingestion of glutathione. The fate of direct oral ingestion of glutathione has been demonstrated in a clinical study showing that 3 grams of glutathione delivered by oral ingestion does not elevate plasma glutathione levels.

Building glutathione level in the body has required the use of either direct intravenous infusion of glutathione or the administration of building blocks of glutathione such as cysteine (Smith et al, U.S. Pat. No. 6,495,170) as the direct oral administration has been documented to neither elevate glutathione levels (Rowe et al, U.S. Pat. No. 5,747,459) nor have clinical benefit.

The intravenous administration of glutathione has been reported to have benefit in improving blood flow in peripheral vascular disease and improving symptoms related to Parkinson's disease. This application includes claims for the use of the invention in its oral form in the treatment of Parkinson's disease, Cystic Fibrosis, vascular disease, diabetes, as well as inflammatory diseases of the respiratory tract such as chronic sinus disease, emphysema and allergy. A particular advantage of this invention is the ability of liposomal encapsulation of glutathione (reduced) is to deliver the reduced glutathione to the intracellular compartment of cells, such as, but not limited to, red blood cells. This characteristic of the invention is important in individuals with defects in the transport of glutathione into cells such as the defect seen in cystic fibrosis.

The clinically effective use of glutathione in its pure form directly without any additive encapsulation or transformation (in the "neat" form) has been limited to the intravenous administration of the biochemical in the reduced state. As glutathione is unstable in solution without the protection from oxidation offered by this invention, there are limitations to the stability of solution preparations. Demopoulus et al, U.S. Pat. No. 6,204,248, describe a method of preparation of glutathione in combination with crystalline ascorbic acid enclosed in a gel cap for oral administration. Demopoulus et al, U.S. Pat. No. 6,204,248 describes the use of the glutathione in combination with crystalline ascorbic acid enclosed in a gel cap for oral administration to alter redox state of cells and improve disease processes. Demopoulus et al, U.S. Pat. No. 6,350,467 references the use of the glutathione in combination with crystalline ascorbic acid enclosed in a gel cap for oral administration to treat additional disease states. A recent patent, Smith, U.S. Pat. No. 6,764,693 references the use of liposomes containing a combination of glutathione in combination with at least one other antioxidant material to increase intracellular and extra cellular antioxidants. There is no claim for the use of liposomal glutathione either individually or in combination with other antioxidants for the treatment of Parkinson's disease or Cystic Fibrosis. Additionally the claim for activity of the liposome in Smith '693 is a population of liposomes suitable for undergoing peroxidation and lysis, releasing their contents into the circulation. The preferred method of composition of the liposome claimed in this invention is for a liposome that functions by fusion and transfer of the glutathione content into cells. Evidence for this method of action is provided in the clinical examples of improvement in the red blood cell level of glutathione paralleling clinical improvement in individuals with Cystic Fibrosis.

A liposome is a microscopic fluid filled pouch whose walls are made of one or more layers of phospholipid materials identical to the phospholipid that make up cell membranes. Lipids can be used to deliver materials such as drugs to the body because of the enhanced absorption of the liposome. The outer wall of the liposome is fat soluble, while the inside is water-soluble. This combination allows the liposome to become an excellent method for delivery of water-soluble materials that would otherwise not be absorbed into the body. A common material used in the formation of liposomes is phosphatidylcholine, the material found in lecithin. A more detailed description of the constituents of this invention is provided.

Cystic Fibrosis (CF) is an inherited disorder that affects approximately 30,000 children in the United States. It is the most common genetic disorder and the largest genetic killer of children. Cystic fibrosis is characterized by the production of thick mucus in the lungs and sinuses and leads to recurring infections as well as gastrointestinal dysfunction. At the present time there is no cure and none of the therapies offered correct the underlying cellular defect. The current therapy is oriented toward strategies for removing mucus with physical therapies and antibiotics therapy for treating the infections that inevitably occur. Even with intensive therapies the current median age of survival of people with CF is the early 30's. Although CF has serious clinical implications for the gastrointestinal and genital tracts, pulmonary disease is the primary cause of death in 90% of CF patients.

Recent research demonstrates that the gene defect in CF codes for a protein that carries materials across cell membranes. This is associated with inability of people with CF to carry chloride into cells, which results in the characteristic of the accumulation of an excess of chlorides on the skin. This observation leads to the initial test characteristic of CF, the sweat chloride test. The protein that carries chloride, the CF transmembrane conductance regulator (CFTR) protein, has also been found to carry other large anions such as glutathione across cell membranes. The lung epithelial lining fluid of adults with CF has lower glutathione levels than controls and laboratory animal studies of mice without the CFTR protein gene confirm the observation that glutathione transport is deficient in CF. In addition, the ratio of reduced to oxidized GSH in CF individuals is abnormal with an excess of oxidized glutathione present. The lack of glutathione transport has led to the observation that oral supplements used to increase glutathione levels may not have the effect of reaching the interior glutathione deficient cells, such as red blood cells (RBC). Thus, the RBC glutathione level has been proposed as a potential marker of disease severity in individuals with cystic fibrosis.

The majority of glutathione is formed in the liver and released into the blood. It appears that the membrane transport defect in cystic fibrosis affects the ability of the red blood cell to maintain adequate levels of glutathione in side of cells such as red blood cells. Thus, more severe cases of cystic fibrosis are associated with a decrease in the red blood cell level of glutathione that exceeds that found in the plasma. The addition of the presently described invention, liposomal glutathione, to the system can raise the level of glutathione inside the cells of the body such as the red blood cells.

Liposomes have been documented to fuse with red blood cells and deliver their content into the cells (Constantinescu I, Artificial cells, blood substitutes, and immobilization biotechnology. 2003 November; 31(4):395-424).

The clinical examples demonstrate that the present invention can raise the glutathione level of red blood cells of individuals with Cystic Fibrosis. As these individual's cells have a genetic defect in the transport of glutathione across cell membranes the increase observed in the red blood cell levels of glutathione is demonstrated to occur after oral ingestion of the invention and by a mechanism such as fusion of the liposome. Release of the glutathione reduced into the systemic circulation would not result in the elevation of glutathione seen in the individuals with Cystic Fibrosis.

Liposomes are able to convey their contents to cells by one of four methods:

Adsorption: The wall of the liposome becomes adherent to the cell and releases the content of the liposome into the cell.

Endocytosis: In endocytosis the cell engulfs the liposome creating an additional lamella around the liposome, which is dissolved inside the cell, releasing the contents of the liposome. In the process of endocytosis a portion of the plasma membrane is invaginated and pinched off forming a membrane-bounded vesicle called an endosome.

Lipid exchange: The lipid contents of the liposome and the cell exchange their lipid contents, releasing the contents of the liposome Fusion: The melding or the liposome membrane with the membrane of the cell, carrying their contents of the liposome into the cell.

One or more of these mechanisms is at play in the described invention, allowing delivery of glutathione into the cells of individuals with cystic fibrosis.

While tableted or other solid forms of administration of nutrients is convenient for many individuals there is a significant segment of the population for whom swallowing a tablet is not possible. This can be due to age, such as the pediatric segment of the population or the other end of the age spectrum, the geriatric population, many of whom find pill swallowing difficult. For this reason, as well as ease of dose calculation, liquid gel delivery of glutathione will be more universally acceptable. Another advantage is that the present invention enables administration of a larger quantity of GSH in a single dose than other forms of non-parenteral administration as well as enabling incremental adjustment of doses for children and adults.

Liposome delivery of glutathione as described in this invention is particularly efficient for providing glutathione across cell membranes, which is critical for the management of Cystic Fibrosis. This disease is a genetic deficiency of the ability to transport certain molecules like glutathione across cell membranes resulting in an intracellular deficiency of glutathione. The difficulties associated with Cystic Fibrosis occur in the early stages of life, a time in which the ingestion of liquids is the only option for the individuals due to their young age.

Parkinson's Disease

Parkinson's disease (PD) is a medical condition associated with the neuro-motor system and characterized by four primary symptoms:

Tremor or trembling in hands, arms, legs, jaw, and face
Rigidity or stiffness of the limbs and trunk
Bradykinesia, or slowness of movement
Postural instability or impaired balance and coordination.

Individuals with Parkinson's disease may have difficulty walking, talking, or completing other simple tasks. The disease is both chronic and progressive. Early symptoms are subtle and occur gradually and often progress.

The brain is the body's communication headquarters. It is the coordinator of information received from the various parts of the sensory system. The brain processes the information in an organized fashion and relays the information to the motor system for movement. This highly organized passage of information can become disrupted with the slightest offset of the assembly-line fashion of the cellular chemical sequence resulting in major abnormalities.

There are two areas of the brain that are specifically related to motor malfunctions, the substantia nigra and the striatum. The substantia nigra is located in the midbrain, halfway between the cerebral cortex and the spinal cord. In healthy people, the substantia nigra contains certain nerve cells, called nigral cells that produce the chemical dopamine. Dopamine travels along nerve cell pathways from the substantia nigra to another region of the brain, called the striatum. In the striatum, dopamine activates nerve cells that coordinate normal muscle activity.

In people with Parkinson disease, nigral cells deteriorate and die at an accelerated rate, and the loss of these cells reduces the supply of dopamine to the striatum. Dopamine is one of the chemical messengers responsible for transmitting signals in the brain and must be balanced with other neurotransmitters such as acetylcholine. Without adequate dopamine, nerve cells of the striatum activate improperly, impairing a person's ability to control muscular functions such as walking, balance, and muscular movement.

It appears that the substancia nigra cells may be particularly vulnerable to oxidation stress. Oxidation stress occurs in the substancia nigra cells because the metabolism of dopamine requires oxidation and can lead to the formation of free radicals from hydrogen peroxide formation. In the presence of metal ions such as iron the hydrogen peroxide can form hydroxyl ions, which can be very damaging to cells. The hydrogen peroxide is normally detoxified by reduced glutathione in the reaction catalyzed by Glutathione peroxidase, thus an increased rate of dopamine turnover or a deficiency of glutathione could lead to oxidative stress. Thus, it appears that free radicals may be one of the important agents responsible for destruction of substantia nigra neurons, leading to Parkinson's disease. While Parkinson's disease has been treated with some success with intravenous infusion of glutathione, there has been no reported success in the use of oral glutathione in the treatment of Parkinson's disease. Sechi G, Deledda M G, Bua G, Satta W M, Deiana G A, Pes G M, Rosati G. Reduced intravenous glutathione in the treatment of early Parkinson's disease, Prog Neuropsychopharmacol Biol Psychiatry, Oct. 20, 1996 (7):1159-70 PMID: 8938817.

The clinical improvement from this invention seen in patients with Parkinson's disease suggests that oral liposomal glutathione is not only available systemically it also is absorbed into the central nervous system.

Several studies have demonstrated a deficiency of the antioxidant biochemical reduced glutathione in substantia nigra cells of individuals with Parkinson's disease. The magnitude of the reduction in glutathione seems to parallel the severity of the disease.

The standard treatment of Parkinson's disease has relied on the replacement of dopamine in a form called levodopa. Levodopa, also known as L-Dopa (from the full name L-3,4-dihydroxyphenylalanine) is a neutral amino acid found naturally in plants and animals and is used to treat the stiffness, tremors, spasms, and poor muscle control of Parkinson's disease. After oral ingestion, levodopa is absorbed through the small intestine. Levodopa's structure enables it to enter the brain, where nerve cells can decarboxylate the levodopa and create dopamine to replenish the brain's dwindling supply. Dopamine cannot be given directly because it doesn't cross the blood-brain barrier, the elaborate meshwork of fine blood vessels and cells that filters blood reaching the brain. Levodopa crosses the blood-brain barrier by way of the large neutral amino acid carrier transport system. When levodopa is taken alone, however, about 95% of it is metabolized to dopamine in the body, before it ever reaches the brain. Instead of being used by the brain the dopamine circulating through the body can produce side effects such as nausea or vomiting before it is broken down in the liver.

To limit side effects, levodopa is usually given in combination with carbidopa to increase the availability and utilization of levodopa. Carbidopa inhibits peripheral decarboxylation of levodopa but not central decarboxylation because it does not cross the blood-brain barrier. Since peripheral decarboxylation is inhibited, this allows more levodopa to be available for transport to the brain, where it will be converted to dopamine, and relieve the symptoms of Parkinson's. Carbidopa and levodopa are given together in medications with the trade names Stalevo (a registered trademark of Orion Pharma Inc.) or Sinemet (a registered trademark of Bristol-Myers-Squibb) and in various generic forms. The addition of carbodopa is so effective that the dose of levodopa must be reduced by 80% when the two are use together. This decreases the incidence of levodopa-induced side effects. When given with carbodopa the half-life of levodopa increases from 1 hr to 2 hr (may be as high as 15 hr in some clients). About 30% of the carbidopa is excreted unchanged in the urine.

Also being used for PD are some dopamine agonists such as pramipexole dihydrochloride sold under the name MIRAPEX (a registered trademark for co-marketing by Boehringer Ingelheim Pharmaceuticals, Inc. and Pfizer, Inc.), which can also be used with the oral liposomal reduced glutathione.

Carbidopa/levodopa lessens the rigidity and slow movement associated with Parkinson's disease, but is less effective in treating tremor or balance problems.

A dilemma that has been noted in recent studies is that the administration of dopamine (singly or in the combined form of carbidopa and levodopa) results in an increase in the formation of free radicals and the continuation of the disease process. Thus, while the administration of levodopa offers amelioration of the symptoms of Parkinson's disease it does not change the underlying mechanisms of free radical formation, oxidation and loss of glutathione intracellular. After several years of use the effectiveness of carbidopa/levodopa decreases and patients need higher and more frequent doses to control their symptoms.

Several studies have demonstrated a deficiency in the antioxidant biochemical called reduced glutathione in specific brain cells associated with movement disorders called the substantia nigra (Pearce R K, Owen A, Daniel S, Jenner P, Marsden C D. Alterations in the distribution of glutathione in the substantia nigra in Parkinson's disease. Journal of Neural Transmission, 1997:104(6-7):661-77. PMID: 9444566).

The magnitude of the decrease of available, functional reduced glutathione inside specific brain cells seems to parallel the severity of the disease. It is theorized that the sequence of events in creating the dopamine loss found in Parkinson's disease involves a more rapid turnover of dopamine in the substancia nigra cells due to an increase in the formation of hydrogen peroxide. The presence of this free radical forming material is apparently associated with either a lack of reduced glutathione or an accumulation of the glutathione in the oxidized state. A publication from Italy in 1996 explored the possibility of therapeutically supporting the glutathione deficient cells with the use of intravenous glutathione. Glutathione was administered intravenously to 9 patients, in the dose of 600 mg twice a day, for 30 days. Patients were treated with the standard therapy using carbodopa-levodopa. It was noted that all patients improved significantly after glutathione therapy, with a 42% decline in disability. The therapeutic benefit lasted for 2-4 months. The authors noted that glutathione has symptomatic efficacy and speculated that glutathione could possibly retard the progression of the disease. No reference was made to reduced glutathione in a liposome (Sechi G, Deledda M G, Bua G, Satta W M, Deiana G A, Pes G M, Rosati G. Reduced intravenous glutathione in the treatment of early Parkinson's disease. Progress in Neuro-psychopharmacology & Biological Psychiatry, Oct. 20, 1996 (7):1159-70. PMID: 8938817).

The problem that this invention solves is to restore the reduced glutathione level in the brain cells associated with Parkinson's disease in a way that can be effectively utilized by patients, and presumably thereby alter the metabolism of dopamine toward normal, allowing a normal response to dopamine. At present no patent claims and no literature suggests the use of liposomal glutathione for the treatment of Parkinson's disease.

A preferred mode of the invention involves administration of sufficient glutathione, reduced, orally via the liposomal glutathione to restore metabolism of dopamine to a functional state. This allows for an improvement in symptoms by allowing the dopamine responsive nigro-striatal cells to respond to lower amounts of available dopamine. When introduced to an individual with Parkinson's disease who is taking levodopa/carbodopa it allows the individual to respond either more efficiently to their current dosing schedule, allowing a lower dose plateau than they would have otherwise. In addition the application of the invention will allow some individuals to respond to lower doses of levodopa/carbodopa. For individuals displaying early symptoms of Parkinson's disease the application of the invention may allow them to delay the need for the administration of levodopa/carbodopa.

Individuals with advancing Parkinson's disease may develop a variety of motor complications associated with levodopa therapy. Fluctuations in motor functions, such as early morning akinesia and "wearing off" are indications for the use of the liposomal glutathione invention.

The invention is a combination for administering a therapeutically effective amount of glutathione orally to an individual with Parkinson's disease, using a liposomal encapsulation of glutathione. Prior to the introduction of this invention, the only method for administering a therapeutically effective amount of glutathione was the intravenous infusion of glutathione. While intravenous infusion is useful for establishing the therapeutic efficacy of glutathione in an individual, the costs and inconvenience of intravenous administration made it extremely difficult to administer repeated doses for continued therapy. The invention is also useful in the same way for the more general class of neurodegenerative diseases like Parkinson's disease.

While there have been reports of intravenous liposome uptake protecting liver cells in animals exposed to material toxic to the liver (Wendel A., Hepatic lipid peroxidation: caused by acute drug intoxication, prevented by liposomal glutathione, International Journal Clinical Pharmacology Research, 1983; 3(6):443-7. PMID: 6678834), there are no previous reports of benefit of oral liposomal glutathione in the treatment of human disease processes nor art claiming the use of oral liposomal glutathione in the treatment of disease states such as Parkinson's disease and Cystic Fibrosis.

Because of its lack of systemic availability from oral administration, glutathione has not been used in an oral form for the treatment of disease states. This invention creates a composition incorporating glutathione which is effective upon administration orally, a method of manufacture of a composition incorporating glutathione which is effective upon administration orally, and is a method of administering reduced glutathione orally, by incorporating the reduced glutathione into a liposome, which increases the absorption of glutathione both from the gastrointestinal tract and into the cells of the body. In addition, the use of the liposome encapsulation prevents or slows the degradation of the active form of glutathione in the reduced state from progressing to the oxidized state before systemic uptake. The method of administration thus improves bio-availability of the glutathione both by absorption, and also by maintaining the active antioxidant state of the reduced glutathione.

The liposome preparations claimed in this invention allows the manufacture of a stable product, which can be used for the administration of glutathione in a form that is convenient. The liposome-glutathione preparation described is also stable from oxidation, allowing a two year, unrefrigerated shelf-life of the product, and has specific characteristics of uptake into cell membranes that improve its therapeutic qualities for certain disease states.

Previous use of liposomes encapsulating glutathione has been limited by concern that the combination would be adversely affected by the acidity and enzymes of the stomach. The preparation used in the present invention is able to deliver therapeutically active amounts of glutathione to the system in spite of these concerns. The invention describes the lipid encapsulation of the glutathione (reduced) into the lipid vesicle of liposomes and administered orally for the transmucosal absorption into the nose, mouth, throat or gastrointestinal tract providing the ability to conveniently supply therapeutically effective amounts of glutathione (reduce). The invention may also be administered topically for dermal and transdermal administration as well as intravenously.

DETAILED DESCRIPTION OF THE PREFERRED EMBODIMENTS

Example 1

Liposomal Glutathione Drink or Spray 2500 mg Per Ounce

|  | % w/w |
| --- | --- |
| Deionized Water | 71.9 |
| Glycerin | 15.00 |
| Polysorbate-20 | 2.50 |
| Lecithin | 1.50 |
| Citrus Seed Extract | 0.50 |
| Potassium Sorbate | 0.10 |
| Glutathione (reduced) | 8.50 |

Components lecithin, ethyl alcohol, cholesterol and glycerin were commingled in a large volume flask and set aside for compounding (Alternatively, in all of the embodiments where the glutathione (reduced) percentage is 8.5, the glutathione (reduced percentage) can be lowered to 8.25 with 0.25% tocopherol acetate added).

In a separate beaker, water, hydroxy citric acid, glycerin, polysorbate 20, glutathione were mixed and heated to 50 degrees C.

The water mixture was added to the lipid mixture while vigorously mixing with a high speed, high shear homogenizing mixer at 750-1500 rpm for 30 minutes.

The homogenizer was stopped and the solution was placed on a magnetic plate, covered with parafilm and mixed with a magnetic stir bar until cooled to room temperature. Citrus seed extract were added and the solution was placed in appropriate dispenser for ingestion as a liquid or spray dispenser.

Analysis of the preparation under an optical light microscope with polarized light at 400× magnification confirmed presence of both multilamellar lipid vesicles (MLV) and unilamellar lipid vesicles.

The preferred embodiment includes the variations of the amount of glutathione to create less concentrated amounts of glutathione. The methods of manufacture described in Keller et al, U.S. Pat. No. 5,891,465 are incorporated into this description.

A variation of the preferred embodiment of the invention is the addition of EDTA (ethylene diamine tetraacetic acid) 100 mg per ounce to be encapsulated in the liposome along with the glutathione.

Example 1A

Liposomal Glutathione Drink or Spray 2500 mg Per Ounce or Form Suitable for Encapsulation or Gel

|  | % w/w |
| --- | --- |
| Deionized Water | 74.4 |
| Glycerin | 15.00 |
| Lecithin | 1.50 |
| Citrus Seed Extract | 0.50 |
| Potassium Sorbate (optional spoilage retardant) | 0.10 |
| Glutathione (reduced) | 8.5 |

A lipid mixture having components lecithin, ethyl alcohol and glycerin were commingled in a large volume flask and set aside for compounding.

In a separate beaker, a water mixture having water, glycerin, glutathione were mixed and heated to 50.degree. C.

The water mixture was added to the lipid mixture while vigorously mixing with a high speed, high shear homogenizing mixer at 750-1500 rpm for 30 minutes.

The homogenizer was stopped and the solution was placed on a magnetic stirring plate, covered with parafilm and mixed with a magnetic stir bar until cooled to room temperature. Normally, citrus seed extract would be added. Normally, a spoilage retardant such as potassium sorbate or BHT would be added. The solution would be placed in appropriate dispenser for ingestion as a liquid or administration as a spray.

Analysis of the preparation under an optical light microscope with polarized light at 400× magnification confirmed presence of both multilamellar lipid vesicles (MLV) and unilamellar lipid vesicles.

The preferred embodiment includes the variations of the amount of glutathione to create less concentrated amounts of glutathione. The methods of manufacture described in Keller et al U.S. Pat. No. 5,891,465 are incorporated into this description.

Example 2

Liposomal glutathione Drink or Spray 1000 mg Per Ounce With EDTA 1000 mg Per Ounce

|  | % w/w |
| --- | --- |
| Deionized Water | 73.55 |
| Glycerin | 15.00 |
| Polysorbate-20 | 2.50 |
| Lecithin | 1.50 |
| Citrus Seed Extract | 0.50 |
| Tocopherol Acetate | 0.25 |
| Potassium Sorbate | 0.10 |
| Glutathione (reduced) | 3.30 |
| EDTA | 3.30 |

Embodiment two of the invention includes the incorporation of the fluid liposome (such as that prepared in Example 1A) into a gelatin based capsule to improve the stability, provide a convenient dosage form, and assist in sustained release characteristics of the liposome. The present embodiment relates to the use of glutathione in the reduced state encapsulated into liposomes or formulated as a preliposome formulation and then put into a capsule. The capsule can be a soft gel capsule capable of tolerating a certain amount of water, a two-piece capsule capable of tolerating a certain amount of water or a two-piece capsule where the liposomes are preformed then dehydrated.

The liposome-capsule unit containing biologically encapsulated material can be taken in addition to orally, used for topical unit-of-use application, or other routes of application such as intra-occular, intranasal, rectal, or vaginal.

The composition of examples 1 and 2 may be utilized in the encapsulated embodiment of this invention.

Gelatin capsules have a lower tolerance to water on their interior and exterior. The usual water tolerance for a soft gel capsule is 10% on the interior. The concentration of water in a liposome formulation can range from 60-90% water. An essential component of the present invention is the formulation of a liposome with a relatively small amount of water, in the range of 5-10%. By making the liposome in a low aqueous system, the liposome is able to encapsulate the biologically active material and the exposure of water to the inside lining of the capsule is limited. The concentration of water should not exceed that of the tolerance of the capsule for which it is intended. The preferred capsule for this invention is one that can tolerate water in the 15-20% range.

The method described by Keller et al, U.S. Pat. No. 6,726,924 are incorporated in this description.

Components are commingled and liposomes are made using the injection method (Lasic, D., Liposomes, Elsevier, 88-90, 1993). When liposome mixture cooled down 0.7 ml was drawn into a 1 ml insulin syringe and injected into the open-end of a soft gelatin capsule then sealed with tweezers. The resulting capsule contains 10 mg CoQ10. Filling of gel caps on a large scale is best with the rotary die method or others such as the Norton capsule machine.

Example 3

Glutathione LipoCap Formulation

| Ingredient | Concentration (%) |
|---|---|
| Sorbitan Oleate | 2.0 |
| Glutathione | 89.8 |
| Purified Water | 4.0 |
| Potassium Sorbate | 0.2 |
| Polysorbate 20 | 2.0 |
| Phospholipon 90 (DPPC) | 2.0 |

Components are commingled and liposomes are made using the injection method (Lasic, D., Liposomes, Elsevier, 88-90, 1993). When liposome mixture cooled down 0.7 ml was drawn into a 1 ml insulin syringe and injected into the open-end of a soft gelatin capsule then sealed with tweezers. The resulting one gram capsule contains 898 IU of Vitamin E. Large scale manufacturing methods for filling gel caps, such as the rotary die process, are the preferred method for commercial applications.

Embodiment number three of the present invention includes the creation of liposome suspension using a self-forming, thermodynamically stable liposomes formed upon the adding of a diacylglycerol-PEG lipid to an aqueous solution when the lipid has appropriate packing parameters and the adding occurs above the melting temperature of the lipid. The method described by Keller et al, U.S. Pat. No. 6,610,322 is incorporated into this description.

Most, if not all, known liposome suspensions are not thermodynamically stable. Instead, the liposomes in known suspensions are kinetically trapped into higher energy states by the energy used in their formation. Energy may be provided as heat, sonication, extrusion, or homogenization. Since every high-energy state tries to lower its free energy, known liposome formulations experience problems with aggregation, fusion, sedimentation and leakage of liposome associated material. A thermodynamically stable liposome formulation which could avoid some of these problems is therefore desirable.

The present embodiment prefers liposome suspensions which are thermodynamically stable at the temperature of formation. The formulation of such suspensions is achieved by employing a composition of lipids having several fundamental properties. First, the lipid composition must have packing parameters which allow the formation of liposomes. Second, as part of the head group, the lipid should include polyethyleneglycol (PEG) or any polymer of similar properties which sterically stabilizes the liposomes in suspension. Third, the lipid must have a melting temperature which allows it to be in liquid form when mixed with an aqueous solution.

By employing lipid compositions having the desired fundamental properties, little or no energy need be added when mixing the lipid and an aqueous solution to form liposomes. When mixed with water, the lipid molecules disperse and self assemble as the system settles into its natural low free energy state. Depending on the lipids used, the lowest free energy state may include small unilamellar vesicle (SUV) liposomes, multilamellar vesicle (MLV) liposomes, or a combination of SUVs and MLVs.

In one aspect, the invention includes a method of preparing liposomes. The method comprises providing an aqueous solution; providing a lipid solution, where the solution has a packing parameter measurement of $P_a$ ($P_a$ references the surface packing parameter) between about 0.84 and 0.88, a $P_v$ ($P_v$ references the volume packing parameter) between about 0.88 and 0.93, (See, D. D. Lasic, Liposomes, From Physics to Applications, Elsevier, p. 51 1993), and where at least one lipid in the solution includes a polyethyleneglycol (PEG) chain; and combining the lipid solution and the aqueous solution. The PEG chain preferably has a molecular weight between about 300 Daltons and 5000 Daltons. Kinetic energy, such as shaking or vortexing, may be provided to the lipid solution and the aqueous solution. The lipid solution may comprise a single lipid. The lipid may comprise dioleolylglycerol-PEG-12, either alone or as one of the lipids in a mixture. The method may further comprise providing an active compound, in this case glutathione (reduced); and combining the active compound with the lipid solution and the aqueous solution.

A variation of embodiment three is the combination of glutathione (reduced) and EDTA.

Additional variations of this embodiment of glutathione (reduced) and the compounds claimed in this invention, including levodopa, carbidopa, Selenium, and EDTA are described in Keller et al, U.S. Pat. No. 6,610,322.

Case Example and Dosing

Liposomal glutathione in Cystic Fibrosis

Case 1. MF aged 4 years has been diagnosed with cystic fibrosis and has the characteristic finding of elevated sweat chloride. She experiences frequent respiratory infections requiring antibiotic therapy and has a chronic cough. Her mother described her as having decreased energy for play, which restricted her physical activity. MF's red blood cell level of glutathione was found to be 136 (normal range 200-400 micromole per L.) in December 2004.

Oral liposomal glutathione reduced was ingested in an amount that provided 300 mg glutathione per dose, with one dose per day for two weeks. After two weeks ingesting the combination the individual's glutathione level was found to be 570 micromole per L. During the interval ingesting the oral liposomal glutathione reduced, the individual was noted to have resolved the clinical symptoms of chronic cough, and to have more energy. Her mother described her as being able to function normally after taking the oral liposomal glutathione. The dose was adjusted down to 150 mg per dose, once a day, and the glutathione level reduced to 240 micromole per L., which has been used for a maintenance dose.

Case 2. Laura B 23 years old with CF manifesting with severe chronic lung disease, and chronic sinus congestion.

Her lung function had been unchanged at a very low level for 2 years.

Baseline RBC GSH was low

Baseline RBC GSH was low at 46 micromole per L. After 3 weeks of therapy the RBC GSH was 246 micromole per L. The normal range of RBC GSH is 200-400 micromole per L.

Clinically, the patient noted a decrease in the amount of mucus secretions in both the sinuses and the lungs as well as an improvement in a cough, which had been chronic.

Case 3.

GF, an 18 month old girl with gastrointestinal manifestation of cystic fibrosis. In the first 12 months of life her growth pattern was normal with her weight in the $50^{th}$ percentile. At the time of initial evaluation the child had fallen to the $25^{th}$ percentile for weight. Her glutathione blood levels were normal. The child was treated with the ingestion of liposomal glutathione in a dose of 100 mg per thirty pounds twice a day.

After three months of ingesting the liposomal glutathione the child's growth had returned to normal with her weight falling into the 50-60$^{th}$ percentile.

Dosing recommendation for the preferred embodiment of the invention, as described in example 1.

Using oral liposomal glutathione 2500 mg per ounce.

Recommended Use 1 ounce is 5.56 teaspoons.

1 teaspoon of oral liposomal glutathione reduced contains approximately 440 mg GSH.

Suggested dose depends on body weight. Recommended amounts are for daily use.

Gently stir liposomal glutathione into the liquid of your choice.

Refrigeration after opening is required to prevent deterioration.

Determine Daily Dose by Body Weight

Under 30 lbs: ¼ teaspoon=110 mg GSH
30-60 lbs: ½ teaspoon=220 mg GSH
60-90 lbs: ¾ teaspoon=330 mg GSH
90-120 lbs: 1 teaspoon=440 mg GSH
120-150 lbs: 1½ teaspoon=660 mg GSH
Over 150 lbs: 2 teaspoons=880 mg GSH Parkinson's Disease:

A preferred application of the invention to Parkinson's disease is to initially observe the response to glutathione therapy using the intravenous infusion of glutathione 1500 mg. One dose of the 1500 mg. glutathione intravenous is administered every 12 to 24 hours for a total of 3 doses and the response to the therapy is observed. If there is a positive indication (improvement in the individual's symptoms of Parkinson's disease) for the continued use of glutathione, the present invention (liposomal glutathione) is utilized as an oral method of maintaining improvement of the Parkinson's symptoms.

Dosing Guide for Levodopa

Carbidopa/Levodopa: Each 10/100 tablet contains: carbidopa, 10 mg, and levodopa, 100 mg.

Each 25/100 tablets contains: carbidopa, 25 mg, and levodopa, 100 mg.

Each 25/250 tablet contains: carbidopa, 25 mg, and levodopa, 250 mg.

Each sustained-release tablet contains: carbidopa, 50 mg, and levodopa, 200 mg.

Case Example 3:

PP is 67-year-old woman with tremor affecting her hands, which is consistent with Parkinson's disease. She relates being affected by the tremor to the point that she has difficulty closing buttons and writing her signature. She was placed on oral liposomal glutathione reduced, 600 mg. twice a week. After three weeks of ingesting the invention, PP was observed to have significant reduction in her tremor. PP was able to fasten her buttons with more ease and was able to write her signature with less shaking.

Dosing Instructions for Liposomal Glutathione in Parkinson's Disease

The preferred initial therapy is the administration of 1.5 teaspoons liposomal glutathione, which contains approximately 660 mg. of glutathione twice a day for two weeks. If there is clinical improvement during this time, the dose may be reduced to the level that maintains the good response on a continuing basis.

If there is no response at two weeks the therapy at the dose of 1.5 teaspoons liposomal glutathione, which contains approximately 660 mg. of glutathione twice a day until the conclusion of the time period, or clinical improvement has been achieved. If there is clinical improvement during this time, the dose may be reduced to the level that maintains the good response on a continuing basis.

An alternative approach is to use the following:

Initial dose 1 ounce=2,500 mg

Repeat every 12 hours for a total or 4 doses.

Observe response and continue with dose that gives clinical response using the following body weight indicator as dosing guide:

| DETERMINE DAILY DOSE BY BODY WEIGHT AND RESPONSE TO THERAPY: | | Reduced glutathione referred to as GSH |
|---|---|---|
| 60-90 lbs: | ¾ teaspoon | 330 mg GSH |
| 90-120 lbs: | 1 teaspoon | 440 mg GSH |
| 120-150 lbs: | 1.5 teaspoon | 660 mg GSH |
| Over 150 lbs: | 2 teaspoons | 880 mg GSH |

The word "Selenium" means the chemical element selenium or pharmaceutically acceptable selenium-bearing compounds. Because Selenium appears to facilitate biochemical cycles involving glutathione, the purpose of Selenium is to be sure that sufficient selenium is present.

What is claimed is:

1. A pharmaceutical composition enabling delivery after oral administration of a therapeutically effective amount of glutathione (reduced) comprising:

a therapeutic dose of a reduced glutathione stabilized in a liposomal pharmaceutical carrier capable of being ingested orally, and capable of delivering glutathione (reduced) in a physiologically active state to improve symptoms in disease states by transfer of the glutathione into animal cells, where the concentration of reduced glutathione in the entrapped aqueous space of the liposomes is about 123 mM.

2. The composition according to claim 1, further comprising:

a pharmaceutically acceptable form of Selenium.

3. The composition according to claim 1, further comprising glycerin.

4. The composition according to claim 3, further comprising:
   a pharmaceutically acceptable form of Selenium.

5. A pharmaceutical composition enabling delivery after oral administration of a therapeutically effective amount of glutathione (reduced) for an individual with cystic fibrosis, comprising:
   a therapeutic dose of reduced glutathione stabilized in a liposomal pharmaceutical carrier capable of being ingested orally, and capable of delivering glutathione (reduced) in a physiologically active state to an individual with cystic fibrosis by transfer of the glutathione into animal cells,
      where the concentration of reduced glutathione in the entrapped aqueous space of the liposomes is about 123 mM.

6. The composition according to claim 5, further comprising:
   a pharmaceutically acceptable form of Selenium.

7. A pharmaceutical composition enabling delivery after oral administration of a therapeutically effective amount of glutathione (reduced) for an individual with cystic fibrosis, comprising:
   an amount given on a daily basis of reduced glutathione stabilized in a liposomal pharmaceutical carrier capable of being ingested orally that raises the red blood cell level of glutathione to a normal range;
      where the concentration of reduced glutathione in the entrapped aqueous space of the liposomes is about 123 mM.

8. The composition according to claim 7, further comprising:
   a pharmaceutically acceptable form of Selenium.

9. A pharmaceutical composition enabling delivery after oral administration of a therapeutically effective amount of glutathione (reduced) for an individual with neurodegenerative disease, including Parkinson's disease, comprising:
   an amount given on a daily basis of reduced glutathione stabilized in a liposomal pharmaceutical carrier capable of being ingested orally that raises the red blood cell level of glutathione to a normal range;
      where the concentration of reduced glutathione in the entrapped aqueous space of the liposomes is about 123 mM.

10. The composition according to claim 9, further comprising:
    a pharmaceutically acceptable form of Selenium.

11. A method of oral administration of reduced glutathione comprising:
    encapsulating in a liposomal pharmaceutical carrier a therapeutic dose of reduced glutathione; and
    administering said carrier to an animal,
       where the concentration of reduced glutathione in the entrapped aqueous space of the liposomes is about 123 mM.

12. The method according to claim 11 where said liposomal pharmaceutical carrier includes glycerin.

13. A method of administration of a therapeutic dose of reduced glutathione in liposomal carrier via oral, nasal, topical, or transmucosally via the gastrointestinal tract comprising:
    encapsulating in a liposomal pharmaceutical carrier a therapeutic dose of reduced glutathione; and
    administering said carrier orally, nasally, topically, or transmucosally via the gastrointestinal tract,
       where the concentration of reduced glutathione in the entrapped aqueous space of the liposomes is about 123 mM.

14. A method of manufacture of a therapeutically effective oral preparation of reduced glutathione comprising:
    encapsulating in a liposomal pharmaceutical carrier a therapeutic dose of reduced glutathione,
       where the concentration of reduced glutathione in the entrapped aqueous space of the liposomes is about 123 mM.

15. The method according to any one of claims 11-13 and 14, further comprising:
    combining into said carrier a therapeutic dose of Selenium.

16. A composition prepared according to claim 14.

* * * * *

UNITED STATES PATENT AND TRADEMARK OFFICE
CERTIFICATE OF CORRECTION

PATENT NO. : 8,349,359 B2  
APPLICATION NO. : 11/163979  
DATED : January 8, 2013  
INVENTOR(S) : Guilford et al.

Page 1 of 1

It is certified that error appears in the above-identified patent and that said Letters Patent is hereby corrected as shown below:

In the Claims

Column 14, Claim 1, line 63, the word "about" should be deleted and the words: --at least-- inserted in its place.

Column 15, Claim 5, line 18 and Claim 7, line 32, in both locations, the word "about" should be deleted and the words: --at least-- inserted in its place.

Column 16, Claim 9, lines 4 and 15, Claim 13, line 28, and Claim 14, line 35, in all locations, the word "about" should be deleted and the words: --at least-- inserted in its place.

Signed and Sealed this  
Twenty-second Day of October, 2013

Teresa Stanek Rea  
*Deputy Director of the United States Patent and Trademark Office*